United States Patent [19]

Böhm et al.

[11] Patent Number: 4,609,760

[45] Date of Patent: Sep. 2, 1986

[54] PROCESS FOR THE PREPARATION OF 2,6-XYLIDINE

[75] Inventors: Siegfried Böhm, Dormagen; Helmut LeBlanc, Waldbroel; Karlfried Wedemeyer, Cologne, all of Fed. Rep. of Germany

[73] Assignee: Bayer Aktiengesellschaft, Leverkusen, Fed. Rep. of Germany

[21] Appl. No.: 270,663

[22] Filed: Jun. 4, 1981

[30] Foreign Application Priority Data

Jun. 24, 1980 [DE] Fed. Rep. of Germany ....... 3023487
Mar. 14, 1981 [DE] Fed. Rep. of Germany ....... 3109986

[51] Int. Cl.$^4$ .............................................. C07C 85/06
[52] U.S. Cl. ..................................... 564/402; 564/403
[58] Field of Search ................................. 564/402, 403

[56] References Cited

U.S. PATENT DOCUMENTS 2,013,873  9/1935  Vogt ..................... 564/402
3,860,650  1/1975  Becker et al. ................ 564/402 X

FOREIGN PATENT DOCUMENTS 1344574  1/1974  United Kingdom ................ 564/402

Primary Examiner—Charles F. Warren
Attorney, Agent, or Firm—Sprung, Horn, Kramer & Woods

[57] ABSTRACT

An improved process for the preparation of 2,6-xylidine by amination of 2,6-dimethylphenol in the vapor phase with ammonia in the presence of an aluminum oxide catalyst is disclosed. According to the invention, particular amination conditions are chosen to effect high yields of the desired product. These conditions include a temperature of 360° to 460° C. and a minimum molar ratio of ammonia to 2,6-dimethylphenol which corresponds to the general formula $$X = e^{(\frac{Y-B}{M})}$$

wherein
X represents the minimum molar ratio of ammonia to 2,6-dimethylphenol,
Y represents the minimum pressure and
M and B are constants, with M = −39.2826 and B = 262.809.

14 Claims, No Drawings

PROCESS FOR THE PREPARATION OF 2,6-XYLIDINE

BACKGROUND OF INVENTION

1. Field of Invention

The invention relates to a process for the preparation of 2,6-xylidine by amination of 2,6-dimethylphenol in the vapour phase with ammonia in the presence of an aluminum oxide catalyst.

2. Discussion of Prior Art

It is known to react phenols in the vapour phase with ammonia under pressure on catalysts containing aluminum oxide to give the corresponding anilines (U.S. Pat. No. 1,935,209, U.S. Pat. No. 2,013,873, U.S. Pat. No. 3,272,865, German Auslegeschrift No. 2,026,053 and German Offenlegungsschrift No. 2,003,842). Although the publications mentioned list a large number of phenols as suitable starting compounds for the reaction, only a few phenols, in particular phenol itself, m- and p-cresol and 3,5-xylenol, are employed in the examples given in the publications (U.S. Pat. No. 3,272,865, U.S. Pat. No. 1,935,209 and U.S. Pat. No. 2,013,873).

According to German Offenlegungsschrift No. 2,516,316 difficulties occur in amination reactions with substituted phenols. It is thus mentioned, for example, that when m-cresol is used, up to 10% of by-products are formed. German Offenlegungsschrift No. 2,516,316 recommends the addition of toluene in order to avoid these disadvantages. 2,6-Substituted phenols have not yet been employed at all in the amination reactions known from the state of the art. The preparation of 2,6-xylidine was hitherto carried out by reacting aluminum tris-(2,6-dimethyl-phenolate) with ammonia at a temperature of about 200° to 500° C. (German Auslegeschrift No. 1,933,636).

In another process (German Auslegeschrift No. 2,208,827) 2,6-dimethylphenol is reacted with ammonia at 200° to 400° C. in the presence of a hydrogen transfer catalyst and in the presence of water and catalytic amounts of a cyclohexanone to give 2,6-xylidene.

On the basis of the steric hindrance by the 2,6-substituents and of the teachings known from German Offenlegungsschrift No. 2,516,316 that o-substituents impede the amination reaction and give rise to the formation of by-products, it is understandable that the amination reaction which is in itself known has not been applied to the preparation of 2,6-xylidine and that the expensive processes according to German Auslegeschrift No. 1,933,636 and German Auslegeschrift No. 2,208,827 have been turned to for the preparation of 2,6-xylidine.

If 2,6-dimethyl-phenol is reacted under the known amination conditions, a comparatively low conversion is indeed also found, and the formation of by-products, in particular isomerization and disproportionation with formation of aniline, o-, m- and p-toluidine, isomeric xylidines and trimethylanilines, is observed to a considerable extent. Thus, the reaction of 2,6-xylenol with ammonia in the gas phase under the amination conditions described in German Auslegeschrift No. 2,026,053 gives, after 50 hours and with 95% conversion, a product mixture containing only about 50% of 2,6-xylidine.

Apart from the loss in yield resulting from the poor selectivity, the considerable amounts of isomeric 2,4- and 2,5-xylidines, in particular, present great difficulties during working up, since 2,4-dimethylaniline, above all, cannot be separated off or can be separated off only with a very high expenditure on distillation.

Even increasing the pressure to the upper limit of 70 bars given in German Auslegeschrift No. 2,026,053 does not give rise to an improvement either in the conversion or in the selectivity when one of the catalysts used in German Auslegeschrift No. 2,026,053 is employed.

SUMMARY OF INVENTION

A process has now been found for the preparation of 2,6-xylidine by amination of 2,6-dimethylphenol in the vapour phase with ammonia in the presence of an aluminum oxide catalyst, which is characterized in that the amination is carried out at temperatures from 360° C. to 460° C. at a minimum molar ratio of ammonia to 2,6-dimethylphenol which corresponds to the general formula $$X = e^{(\frac{Y-B}{M})}$$

wherein
X represents the minimum molar ratio of ammonia to 2,6-dimethylphenol,
e represents the natural logarithm
Y represents the minimum pressure in bars and
M and B are constants, with M = −39.2826 and B = 262.809.

The process according to the invention is carried out at a molar ratio of ammonia to 2,6-dimethylphenol of at least about 3:1 and under a minimum pressure of about 70 bars. The upper limits both of the ammonia/2,6-dimethylphenol molar ratio and of the pressure are only set by industrial and economic considerations. Nevertheless, if the process is carried out under increased pressure, care must be taken that the ammonia/2,6-dimethylphenol mixture in the reactor is still in the vapour form and is not already liquid. In general, the process according to the invention is carried out at a molar ratio of ammonia to 2,6-dimethylphenol of 3:1 to 140:1, preferably 5:1 to 75:1, and under pressures of 70 to 250 bars, preferably 90 to 220 bars.

In industrial plants, it is advisable to carry out the amination under high pressures, so that only small amounts of ammonia have to be employed and expensive recovery treatment of ammonia can in this way be avoided.

From the abovementioned formula, for example, a chosen ammonia/2,6-dimethylphenol molar ratio of 15:1, 30:1, 70:1 or 75:1 gives a corresponding minimum pressure of 156, 129, 96 or 93 bars which is required, with the given amounts of ammonia, in order to keep the content of isomeric xylidines below 1% at complete conversion of 2,6-dimethylphenol.

The process according to the invention is usually carried out at temperatures from 360° to 460° C., preferably at 380° to 440° C. and particularly preferably at 400° to 430° C.

Catalysts which have proved suitable are aluminum oxide catalysts which contain at least 95% by weight of aluminum oxide, such as $\gamma$-Al$_2$O$_3$ and $\gamma$-Al$_2$O$_3$ which contains up to 50% by weight of $\delta$- and $\theta$-Al$_2$O$_3$, less than 0.5% of sodium oxide and less than 0.5% of iron oxide. A highly pure aluminum oxide catalyst which contains at most 0.2% by weight of alkali metal (given as alkali metal oxide) and at most 0.3% by weight of iron metal (given as iron oxide) is preferably employed. A highly pure aluminum oxide catalyst from BASF coded D 10-10 (BASF Company Publication: BASF-Katalysatoren (BASF Catalysts), K 0020 d, e, f 2.74, page 27) or the aluminum catalysts from Rhône Progil coded SAS 350, SCS 250 and SCS 100 (Rhône Progil Company Publication: Alumina Catalyst Carries SPHERALITE 09.73.10) is particularly preferred.

The aluminum oxide catalysts to be employed can be used in the form of tablets or beads, and tablets with a diameter of about 1.5 mm to about 10 mm are preferably employed.

The process according to the invention can be carried out, for example as follows:

The 2,6-dimethylphenol and an excess of ammonia are passed through the reaction tube, which is filled with the aluminum oxide catalyst, under pressure and at elevated temperatures. After the reaction tube, the reaction mixture is let down and condensed. The condensate is subjected to fractional distillation in a manner which is in itself known. To recycle the unreacted ammonia content, the ammonia can be distilled off from the product mixture under about 50 bars and circulated.

In a preferred embodiment of the process according to the invention, water is added during the reaction. In general, it is expedient to add up to 15% by weight of water, relative to the amount of ammonia employed and to the amount of 2,6-dimethylphenol. 5 to 10% by weight of water is preferably added. The selectivity of the reaction can be improved further by this preferred procedure.

The process according to the invention can be carried out either discontinuously or continuously.

Surprisingly, it is possible to prepare 2,6-xylidine which is virtually free from troublesome isomeric 2,4-xylidine and 2,5-xylidine with the aid of the process according to the invention, which guarantees isolation of the 2,6-xylidine in a purity of over 99% without difficulty.

2,6-Xylidine is an intermediate product for the preparation of herbicides (compare German Offenlegungsschrift No. 2,648,008, German Offenlegungsschrift No. 2,305,495 and U.S. Pat. Nos. 3,952,056 and 4,019,894). The herbicides can be prepared, for example, by acylation and etherification of 2,6-xylidine.

The process according to the invention may be illustrated with the aid of the examples which follow.

(A) ALUMINUM OXIDE CATALYST

1. $\gamma$-Al$_2$O$_3$ tablet with a diameter of 10 to 15 mm. Surface: 230 m$^2$/g.
Composition of the dry catalyst:
Al$_2$O$_3$: 99%
Na$_2$O: 0.2%
Fe$_2$O$_3$: 0.3%

2. $\gamma$-Al$_2$O$_3$ beads with a diameter of 2 to 5 mm. Surface: 350 m$^2$/g.
Composition of the catalyst:
Al$_2$O$_3$: 99%
Na$_2$O: 0.7%
Fe$_2$O$_3$: 0.025%
SiO$_2$: 0.02%

3. $\gamma$-Al$_2$O$_3$ beads with a diameter of 4 to 6 mm. Surface: 275 m$^2$/g.
Composition of the catalyst:
Al$_2$O$_3$: 99%
Na$_2$O: 0.08%
Fe$_2$O$_3$: 0.025%
SiO$_2$: 0.02%

4. $\gamma$-Al$_2$O$_3$ beads with a diameter of 2 to 4 mm. Surface: 80 to 100 m$^2$/g.
Composition of the catalyst:
Al$_2$O$_3$: 99%
Na$_2$O: 0.08%
Fe$_2$O$_3$: 0.025%
SiO$_2$: 0.02%

5. $\gamma$-Al$_2$O$_3$ beads with a diameter of 2 to 3 mm. Surface: 390 m$^2$/g.
Composition of the dry catalyst:
Al$_2$O$_3$: 96.5%
Na$_2$O: 1.5%
Fe$_2$O$_3$: 0.1%
SiO$_2$: 1.8%

(B) PREPARATION OF 2,6-XYLIDINE

Example 1

A reactor tube is charged with 880 ml of $\gamma$-Al$_2$O$_3$ tablets with the composition in A 1, and is heated to 400° C. 2,6-Dimethyl-phenol at a rate of 37.5 (=0.31 mol) of xylenol per hour and ammonia at a rate of 313.4 g (=18.4 mol) of NH$_3$ per hour are pumped through steel capillaries, which are likewise kept at 400° C., into the hot reactor, a pressure of 190 bars being established in the reactor with the aid of a pressure-maintaining valve.

The gas mixture issuing from the valve is condensed and collected in a receiver; in order to circulate the ammonia, the excess NH$_3$ is distilled off from the product mixture under a lower pressure (about 50 bars) and condensed and the liquefied ammonia is recycled into the reaction.

34.1 g of 2,6-xylidine are obtained per hour.

After 50 hours, the product mixture, from which the water of reaction has been separated off, contains: 90.8% of 2,6-dimethyl-aniline, 0.1% of 2,4-dimethylaniline, 0.2% of 2,5-dimethyl-aniline, 0.2% of 2,6-dimethyl-phenol and 8.2% of aniline and anilines which are monosubstituted or polysubstituted by methyl.

Example 2

The procedure from Example 1 is repeated, except that 20.1 g (0.16 mol) of 2,6-dimethyl-phenol per hour and 125.9 g (7.4 mols) of ammonia per hour are pumped through 800 ml of the catalyst having the composition in A 1. A pressure of 190 bars is maintained in the reactor at a temperature of 400° C.

18.8 g of 2,6-xylidine are obtained per hour.

The product mixture removed after 50 hours is composed of 93.6% of 2,6-dimethyl-aniline, 0.1% of 2,4-dimethyl-aniline, 0.1% of 2,5-dimethyl-aniline, 0.2% of 2,6-dimethyl-phenol and 5.5% of aniline as well as anilines which are monosubstituted or polysubstituted by methyl.

Example 3

The procedure from Example 1 is repeated, except that 17.5 g (0.14 mol) of 2,6-dimethyl-phenol per hour and 146.4 g (8.6 mols) of ammonia per hour are pumped through 880 ml of the catalyst having the composition in A 1. A pressure of 160 bars is maintained in the reactor at a temperature of 400° C.

15.8 g of 2,6-dimethyl-aniline are obtained per hour.

The product mixture removed after 50 hours is composed of 90.0% of 2,6dimethyl-aniline, 0.2% of 2,4-dimethyl-aniline, 0.2% of 2,5-dimethyl-aniline, 0.2% of 2,6-dimethyl-phenol and 8.9% of aniline as well as anilines which are monosubstituted or polysubstituted by methyl.

Example 4

The procedure from Example 1 is repeated, except that 24.4 g (0.2 mol) of 2,6-dimethyl-phenol per hour and 305.7 g (18.0 mols) of $NH_3$ per hour are pumped through 880 ml of the catalyst having the composition in A 1. A pressure of 130 bars is kept in the reactor at a temperature of 400° C.

21.7 g of 2,6-xylidine are obtained per hour.

The product mixture removed after 50 hours is composed of 89.1% of 2,6-dimethyl-aniline, 0.3% of 2,4-dimethyl-aniline, 0.3% of 2,5-dimethyl-aniline, 0.3% of 2,6-dimethyl-phenol and 9.3% of aniline as well as anilines which are monosubstituted or polysubstituted by methyl.

Example 5

The procedure from Example 1 is repeated, except that 29.8 g (0.24 mol) of 2,6-dimethyl-phenol per hour and 249.2 g (14.7 mols) of $NH_3$ per hour are pumped through 880 ml of the catalyst having the composition in A 2. A pressure of 190 bars is maintained in the reactor at a temperature of 400° C.

21.5 g of 2,6-xylidine are obtained per hour.

The product mixture removed after 50 hours is composed of 72.0% of 2,6-dimethyl-aniline, 0.7% of 2,4-dimethyl-aniline, 0.2% of 2,5-dimethyl-aniline, 11.6% of 2,6-dimethyl-phenol and 13.2% of aniline as well as anilines which are monosubstituted or polysubstituted by methyl.

Example 6

The procedure from Example 1 is repeated, except that 19.0 g (0.16 mol) of 2,6-dimethyl-phenol per hour and 159.3 g (9.4 mols) of $NH_3$ per hour are pumped through 880 ml of the catalyst having the composition in A 3. A pressure of 190 bars is maintained in the reactor at a temperature of 400° C.

14.8 g of 2,6-xylidine are obtained per hour.

The product mixture removed after 50 hours is composed of 77.8% of 2,6-dimethyl-aniline, 0.5% of 2,4-dimethyl-aniline, 0.1% of 2,5-dimethyl-aniline, 9.0% of 2,6-dimethyl-phenol and 11.2% of aniline as well as anilines which are monosubstituted or polysubstituted by methyl.

Example 7

The procedure from Example 1 is repeated, except that 10.1 g (0.08 mol) of 2,6-dimethyl-phenol per hour and 84.8 g (5.0 mols) of $NH_3$ per hour are pumped through 880 ml of the catalyst having the composition in A 4. A pressure of 190 bars is maintained in the reactor at a temperature of 400° C.

8.6 g of 2,6-xylidine are obtained per hour.

The product mixture removed after 50 hours is composed of 84.5% of 2,6-dimethyl-aniline, 0.5% of 2,4-dimethyl-aniline, 0.2% of 2,5-dimethyl-aniline, 0.7% of 2,6-dimethyl-phenol and 13.5% of aniline as well as anilines which are monosubstituted or polysubstituted by methyl.

Example 8

A reactor tube is charged with 1,200 ml of $\gamma$-$Al_2O_3$ tablets having the composition in A 1, and is heated to 400° C.

A solution of 732 g (6 mols) of 2,6-dimethylphenol in 6,120 g (360 mols) of ammonia and 686 g (38.1 mol) of water is pumped from a stock vessel via an ascending tube through a capillary heated to 400° C. into the hot reactor at a rate of 377 g (22.2 mols) of $NH_3$ or 45.1 g (0.37 mol) of xylenol per hour, a pressure of 190 bars being established in the reactor with the aid of a pressure-maintaining valve.

The gas mixture issuing from the valve is condensed and collected in a receiver; to recover the excess ammonia, the unreacted $NH_3$ is distilled off from the product mixture at a lower pressure (about 50 bars).

41.7 g of 2,6-xylidine are obtained per hour. The product mixture removed after 50 hours is composed of 92.3% of 2,6-dimethyl-aniline, 0.1% of 2,4-dimethylaniline, 0.1% of 2,5-dimethylaniline, 1.8% of 2,6-dimethylphenol and 5.6% of aniline as well as anilines which are monosubstituted or polysubstituted by methyl.

(C) COMPARISON EXAMPLES ACCORDING TO GERMAN AUSLEGESCHRIFT NO. 2,026,053

Example 9

The procedure from Example 1 is repeated, except that 10.6 g (0.09 mol) of 2,6-dimethyl-phenol per hour and 29.5 g (1.7 mols) of $NH_3$ per hour are pumped through 880 ml of the catalyst having the composition in A 1. ($NH_3$/xylenol=20:1).

A pressure of 17 bars is maintained in the reactor at a temperature of 380° C.

5.3 g of 2,6-xylidine are obtained per hour.

The product mixture removed after 50 hours is composed of 49.7% of 2,6-dimethyl-aniline, 6.0% of 2,4-dimethyl-aniline, 3.4% of 2,5-dimethylaniline, 4.2% of 2,6-dimethyl-phenol and 32.7% of aniline as well as anilines which are monosubstituted or polysubstituted by methyl.

Example 10

The procedure from Example 1 is repeated, except that 7.8 g (0.06 mol) of 2,6-dimethyl-phenol per hour and 21.8 g (1.3 mols) of $NH_3$ per hour are pumped through 880 ml of the catalyst having the composition in A 5 ($NH_3$/xylenol=20:1).

A pressure of 70 bars is maintained in the reactor at a temperature of 380° C.

3.1 g of 2,6-xylidine are obtained per hour.

The product mixture removed after 50 hours is composed of 39.4% of 2,6-dimethyl-aniline, 11.1% of 2,4-dimethyl-aniline, 0.5% of 2,5-dimethyl-aniline, 3.2% of 2,6-dimethyl-phenol and 42.7% of aniline as well as anilines which are monosubstituted or polysubstituted by methyl.

What is claimed is:

1. A process for the preparation of 2,6-xylidine by contacting 2,6-dimethylphenol with ammonia in the vapor phase in the presence of an aluminum oxide catalyst, the improvement which comprises carrying out the amination at a temperature from 360° to 460° C. at a minimum molar ratio of ammonia to 2,6-dimethylphenol which corresponds to the general formula $$X = e^{(\frac{Y-B}{M})}$$

wherein
X represents the minimum molar ratio of ammonia to 2,6-dimethylphenol,
Y represents the pressure in bars at which the reaction is conducted, it being at least 70 bars and
e represents the natural logarithm.

M and B are constants, with $M = -39.2826$ and $B = 262.809$.

2. A process according to claim 1, wherein the molar ratio of ammonia to 2,6-dimethylphenol is at least 3:1.
3. A process according to claim 2, wherein the amination is carried out at temperatures from 380° to 440° C.
4. A process according to claim 2, wherein the amination is carried out at a temperature from 400° to 430° C.
5. A process according to claim 2, wherein the amination is carried out with a molar ratio of ammonia to 2,6-dimethylphenol of 3–140:1.
6. A process according to claim 2, wherein the amination is carried out at molar ratios of ammonia to 2,6-dimethylphenyl of 5–75:1.
7. A process according to claim 2, wherein the amination is carried out at pressures of 70 to 250 bars.
8. A process according to claim 2, wherein the amination is carried out under a pressure of 90 to 220 bars.
9. A process according to claim 2, wherein the amination is carried out in the presence of up to 15% by weight water, relative to the amount of ammonia employed, and to the amount of 2,6-dimethylphenol.
10. A process according to claim 2, wherein the amination is carried out in the presence of 5 to 10% by weight of water, relative to the amount of ammonia employed and to the amount of 2,6-dimethylphenol.
11. A process according to claim 1, wherein said catalyst consists essentially of alumina.
12. A process according to claim 11, wherein the catalyst contains at least 95% by weight $Al_2O_3$.
13. A process according to claim 11, wherein the catalyst contains less than 0.5% by weight sodium oxide.
14. A process according to claim 11, wherein the catalyst contains less than 0.5% by weight iron oxide.

* * * * *